(12) United States Patent
Song et al.

(10) Patent No.: US 12,125,209 B2
(45) Date of Patent: Oct. 22, 2024

(54) METHOD AND SYSTEM FOR SEGMENTING OVERLAPPING CYTOPLASM IN MEDICAL IMAGE

(71) Applicant: THE HONG KONG POLYTECHNIC UNIVERSITY, Hong Kong (CN)

(72) Inventors: Youyi Song, Hong Kong (CN); Jing Qin, Hong Kong (CN)

(73) Assignee: THE HONG KONG POLYTECHNIC UNIVERSITY, Hong Kong (CN)

( * ) Notice: Subject to any disclaimer, the term of this patent is extended or adjusted under 35 U.S.C. 154(b) by 439 days.

(21) Appl. No.: 17/596,382

(22) PCT Filed: Jun. 18, 2019

(86) PCT No.: PCT/CN2019/091761
§ 371 (c)(1),
(2) Date: Dec. 9, 2021

(87) PCT Pub. No.: WO2020/252665
PCT Pub. Date: Dec. 24, 2020

(65) Prior Publication Data
US 2022/0237782 A1 Jul. 28, 2022

(51) Int. Cl.
*G06T 7/11* (2017.01)
*G06T 7/00* (2017.01)
(Continued)

(52) U.S. Cl.
CPC .............. *G06T 7/11* (2017.01); *G06T 7/0012* (2013.01); *G06T 7/136* (2017.01); *G06V 10/26* (2022.01);
(Continued)

(58) Field of Classification Search
None
See application file for complete search history.

(56) References Cited

U.S. PATENT DOCUMENTS

2019/0272638 A1* 9/2019 Mouton .................. G06T 7/174

OTHER PUBLICATIONS

Song et. al., Segmentation of Overlapping Cytoplasm in Cervical Smear Images via Adaptive Shape Priors Extracted From Contour Fragments IEEE Transactions on Medical Imaging 08; Aug. 5, 2019, vol. 38 Issue 12; pp. 2849-2855.
(Continued)

*Primary Examiner* — Leon Flores
(74) *Attorney, Agent, or Firm* — S&F/WEHRW

(57) ABSTRACT

The present invention relates to a method for segmenting overlapping cytoplasm in a medical image, including: establishing a cytoplasm shape hypothesis set (201); and selecting a shape hypothesis for each cytoplasm from the established cytoplasm shape hypothesis set to perform constrained multi-shape evolution (202), thereby segmenting overlapping cytoplasm in the medical image, wherein the constrained multi-shape evolution (202) includes: segmenting a clump area composed of a plurality of overlapping cytoplasm to provide clump evidence (301); performing shape alignment to assess quality of the selected shape hypotheses (302); and performing shape evolution to determine a better shape hypothesis for each cytoplasm (3). The present invention further relates to a system for segmenting overlapping cytoplasm in a medical image. The method and system of the present invention can perform shape prior-based overlapping cytoplasm segmentation more accurately and more effectively.

14 Claims, 6 Drawing Sheets

(51) Int. Cl.
  *G06T 7/136*    (2017.01)
  *G06V 10/26*    (2022.01)
  *G16H 30/40*    (2018.01)
(52) U.S. Cl.
  CPC ... *G16H 30/40* (2018.01); *G06T 2207/30024* (2013.01)

(56) References Cited

OTHER PUBLICATIONS

Tareef et. al., Automatic segmentation of overlapping cervical smear cells based on local distinctive features and guided shape deformation Neurocomputing 221:94-107.

* cited by examiner

METHOD AND SYSTEM FOR SEGMENTING OVERLAPPING CYTOPLASM IN MEDICAL IMAGE

CROSS-REFERENCE TO RELATED APPLICATIONS

This application is the National Stage of International Application No. PCT/CN2019/091761 filed Jun. 18, 2019.

TECHNICAL FIELD

The present invention relates to a method and system for segmenting overlapping cytoplasm in a medical image, and more particularly, to a method and system for segmenting overlapping cytoplasm in a medical image for cervical cancer screening.

BACKGROUND

Cervical cancer ranks fourth in the mortality rate of malignant tumors in women, and it is also the fourth cancer in incidence. High-quality cervical cancer screening can greatly reduce the incidence and mortality of cervical cancer. Specifically, cervical cancer screening refers to examining the abnormality of each cervical cell sampled from the cervix and placed on a glass slide under a microscope to assess whether there are cervical cancer cells.

For the development of an automatic cervical cancer screening system, segmentation of the overlapping cytoplasm of the cells in the cervical image is one of the key tasks, because in order to examine the abnormality of the cells, the characteristics of the cell level (e.g., the shape and size of the cells, and the area ratio of cytoplasm to nucleus) are clinically important. However, since the intensity (or color) information in an overlapping area is usually confusing and even misleading, the lack of such intensity (or color) information makes this task very challenging.

The traditional method of segmenting overlapping cytoplasm in a medical image is achieved by leveraging the intensity information between the cytoplasm of cells in a clump or combining spatial information. This objective is generally achieved by extending typical segmentation models, such as threshold segmentation, watershed segmentation, and image segmentation. These methods theoretically hypothesize that the intensity information is sufficient to identify an occluded boundary part. However, this hypothesis is flawed. In fact, the intensity information of the overlapping area is usually confusing and even misleading.

In order to eliminate the problems caused by insufficient strength information, shape prior-based methods show a good segmentation performance because additional shape information is inserted into segmentation methods. These methods either use simple shape estimation (for example, the cytoplasm has an elliptical or star shape), or match shape instances from a finite set of shapes collected in advance to model a priori shape. Then, by leveraging the intensity information, the segmentation result needs to be as similar as possible to the modeled prior shape to segment the overlapping cytoplasm. It is usually realized by an active contour model or a level set model, where the prior shape is designed as a regular term in an energy function, and it is assumed that the minimum (or maximum) value of the energy function is obtained by a segmentation function that produces the optimal segmentation result.

Although the prior art has improved the accuracy of segmentation, these existing prior shape methods still have three main shortcomings. First of all, these methods use finite shape hypothesis (for example, shape speculation or collected shape instances) to model prior shapes. Because these specific shape hypotheses cannot well restore the occluded boundary part of the cytoplasm, the prior shapes modeled by these methods are usually not enough to identify the occluded boundary part of the cytoplasm. Second, these methods only use the local prior shape (i.e. the prior information is only the shape of a single cytoplasm) to evolve the shape of the cytoplasm, without considering the shape relationship between all cytoplasm and clumps. As a result, the segmentation results of these methods are usually inconsistent with the clump evidence, and the segmented cytoplasm boundary is deviated from the ideal boundary of the clump. Third, although these methods require the final shape to be as similar as possible to the modeled prior shape, these methods do not impose shape constraints on the final shape. In fact, these methods try to find a suitable compromise between the intensity evidence and the local prior shape by balancing the parameters. Therefore, when the intensity evidence contradicts the local prior shape, these methods will produce incredible segmentation results.

In addition, for the establishment of an infinite shape hypothesis set, existing technologies (e.g., T F Cootes, C J Taylor, and et al. D H Cooper. "Active shape models—their training and application", *Computer Vision and Image Understanding*, 61(1): 38-59, 1995) disclosed relevant content. Although this method can obtain an infinite shape hypothesis set by selecting infinite values, its main disadvantage lies in that it is difficult to collect a set of shape instances to ensure that the invisible cytoplasm shape is well restored by the established shape hypothesis. In the prior art, the establishment of the shape hypothesis set depends on how to collect good shape instances. Usually, it is necessary to manually select representative shape instances. This is an experimental and error-prone way, and it is also a labor-intensive method. This method is not feasible when an infinite number of instances need to be collected to approximate complex shapes.

SUMMARY

Therefore, a technical problem to be solved by the present invention is to provide a method and system that can more accurately and effectively segment overlapping cytoplasm in a medical image based on the prior shape.

In an embodiment, the present invention relates to a method for segmenting overlapping cytoplasm in a medical image, including: establishing a cytoplasm shape hypothesis set; and selecting a shape hypothesis for each cytoplasm from the established cytoplasm shape hypothesis set to perform constrained multi-shape evolution, thereby segmenting overlapping cytoplasm in the medical image, wherein the constrained multi-shape evolution includes: segmenting a clump area composed of a plurality of overlapping cytoplasm to provide clump evidence; performing shape alignment to assess quality of the selected shape hypotheses; and performing shape evolution to determine a better shape hypothesis for each cytoplasm.

The method for segmenting overlapping cytoplasm in a medical image further includes a step of learning the importance of shape instances for updating cytoplasm shape instances for the established cytoplasm shape hypothesis set.

Preferably, the shape alignment and the shape evolution are performed iteratively, an output of the shape alignment is used as an input of the shape evolution, and an output of the shape evolution is used as an input of the shape alignment. The shape alignment assesses whether to start a new shape evolution or not, and once it is determined that no new shape evolution is required, a current shape hypothesis after the shape alignment is regarded as a segmentation result of the overlapping cytoplasm.

Preferably, the cytoplasm shape hypothesis set is established with a formula as follows:

$$\mathcal{H}_s = \{s_i; s_i = \mu + Mx_i, i \in \mathbb{N}\}$$

where $\mu$ represents an average shape of collected shape instances, $Mx_i$ represents a linear combination of eigenvectors of a covariance matrix of the collected shapes, wherein each column of the matrix M represents an eigenvector, $x_i$ represents a weight vector of the linear combination, and $s_i$ represents a shape hypothesis marked as i.

Preferably, the shape alignment includes filling the shape hypotheses selected from the cytoplasm shape hypothesis set to obtain a binary image, and obtaining a rotation angle and a scaling size required for aligning the binary image with the corresponding cytoplasm with a formula as follows:

$$\arg\max(B_i \cap B_c), \text{ s. t. } B_i \subset B_c$$

where $B_c$ represents an image of the segmented clump area; $B_i$ represents an alignment result image, $B_i$ is a binary image with the same size as $B_c$, and $B_i$ should be inside $B_c$.

Preferably, the shape evolution includes: setting an objective function, the objective function being as follows:

$$\mathbb{E}(B_c, x^k) = \sum_{(x,y) \in \Omega_B} (B_g(x,y) - B_c(x,y))^2$$

where x represents set $\{x_i\}_{i=1}^N$ and $x^k$ represents x in the k-th evolution; N represents quantity of cytoplasm in the clump area; $B_g = \cup_{i=1}^N B_i$ represents a binary image generated by an alignment result $\{B_i\}_{i=1}^N$; (x, y) represents coordinates of a pixel in the image; and determining $x^{k+1}$ that causes $\mathbb{E}$ to have a lower value than $x^k$.

Preferably, the determining of $x^{k+1}$ that causes $\mathbb{E}$ to have a lower value than $x^k$ comprises: for matrix p obtained from the objective function, obtaining the following formula according to Taylor's theorem:

$$\mathbb{E}_{(x^k+p)} = \mathbb{E}_{(x^k)} + \nabla \mathbb{E}_{(x^k)}^T p + \tfrac{1}{2} p^T \nabla^2 \mathbb{E}_{(x^k+\gamma p)} p$$

where $\nabla$ and $\nabla^2$ respectively represent a gradient and Hessian matrix calculation; $\gamma$ represents a scalar in an interval (0, 1), and then a minimum value of an overall area of $\mathbb{E}$ in an area formed with $x^k$ as a center of a circle and $\|p\|_2$ as a radius is obtained; returning to $x^k$ to approximate $\mathbb{E}$ as follows:

$$m_k(p) = \mathbb{E}_{(x^k)} + \nabla \mathbb{E}_{(x^k)}^T p + \tfrac{1}{2} p^T \nabla^2 \mathbb{E}_{(x^k)} p$$

where $m_k$ represents $\mathbb{E}$ at $x^k$; approximating the minimum value of $\mathbb{E}$ by the minimum value of $m_k$, and solving the following formula by a trust region method:

$$p^* = \underset{p \in \Omega_p}{\arg\min}\, m_k(p),\ \text{s.t.}\ \|p\|_2 \leq \Delta_k;$$

and obtaining an output result of the k-th evolution as follows:

$$x^{k+1} = x^k + p^*.$$

Preferably, the step of learning the importance of shape instances includes: randomly selecting a set of shape instances and calculating an average shape of the set of shape instances with a formula as follows:

$$\mu = \frac{1}{W} \sum_{i=1}^{K_s} \omega_i s_i$$

where $K_s$ represents a number of selected shape instances; $\omega_i$ represents the importance of each shape instance $s_i$; W represents a sum of all $\omega_i$; and calculating the covariance matrix according to the obtained $\mu$ as follows:

$$M_c = \frac{1}{K_s} \sum_{i=1}^{K_s} (s_i - \mu)(s_i - \mu)^T$$

where a first t eigenvectors of the matrix $M_c$ constitute a matrix $M = (e_1\ e_2\ \ldots\ e_t)$, and their corresponding eigenvalues are $\lambda_1 \geq \lambda_2 \geq \ldots \geq \lambda_t$.

Preferably, if the segmentation result obtained by the constrained multi-shape evolution is greater than a predetermined threshold, recalculation is performed by the step of learning the importance of shape instances to update the shape hypothesis set; and the update is stopped until the segmentation result cannot decrease any more or reaches the predetermined threshold.

According to another aspect, the present invention further relates to a system for segmenting overlapping cytoplasm in a medical image, including: a shape hypothesis set module configured to establish a cytoplasm shape hypothesis set; and a multi-shape evolution module configured to select a shape hypothesis for each cytoplasm from the established cytoplasm shape hypothesis set to perform constrained multi-shape evolution, thereby segmenting overlapping cytoplasm in the medical image, wherein the multi-shape evolution module is configured to: segment a clump area composed of a plurality of overlapping cytoplasm to provide clump evidence; perform shape alignment for assessing quality of the selected shape hypotheses; and perform shape evolution for determining a better shape hypothesis for each cytoplasm.

Preferably, the system for segmenting overlapping cytoplasm in a medical image further includes a shape instance importance learning module configured to update cytoplasm shape instances for the established cytoplasm shape hypothesis set.

Preferably, the shape instance importance learning module is configured to: randomly select a set of shape instances and calculate an average shape of the set of shape instances with a formula as follows:

$$\mu = \frac{1}{W} \sum_{i=1}^{K_s} \omega_i s_i$$

where $K_s$ represents a number of selected shape instances; $\omega_i$ represents the importance of each shape instance $s_i$; W represents a sum of all $\omega_i$; and calculate the covariance matrix according to the obtained $\mu$ as follows:

$$M_c = \frac{1}{K_s}\sum_{i=1}^{K_s}(s_i - \mu)(s_i - \mu)^T$$

where a first t eigenvectors of the matrix $M_c$ constitute a matrix $M=(e_1\ e_2\ \ldots\ e_t)$, and their corresponding eigenvalues are $\lambda_1 \geq \lambda_2 \geq \ldots \geq \lambda_t$.

Preferably, if the segmentation result obtained by the constrained multi-shape evolution module is greater than a predetermined threshold, recalculation is performed by the shape instance importance learning module to update the shape hypothesis set; and the update is stopped until the segmentation result cannot decrease any more or reaches the predetermined threshold. According to the method and system of the present invention, an infinite shape hypothesis set is used to model prior shapes, and in the meanwhile local prior shapes and overall prior shapes are combined with intensity information for evolution, and the result shape in each evolution is constrained to the shape hypothesis set. Compared with the existing method and system for segmenting overlapping cytoplasm in a medical image, the method and system of the present invention can better identify the occluded boundary part, thereby better segmenting the overlapping cytoplasm and providing more accurate shape characteristics for medical diagnosis. The infinite shape hypothesis set established in the present invention can better describe all possible shapes of the cytoplasm, thereby more efficiently segmenting overlapping cytoplasm of different shapes. The constrained multi-shape evolution algorithm of the present invention combines the local prior shapes and the overall prior shapes with intensity information for evolution by considering the shape relationship between all cytoplasm and the entire clump, thereby obtaining more information for segmentation. The present invention uses the importance of each shape instance in the calculation of shape statistics, so that invisible shapes can be well approximated by the shape hypotheses in the shape hypothesis set. The implantation of a learning step in the multi-shape evolution step of the present invention can obtain useful information more effectively. Therefore, compared with the prior art, the method and system of the present invention for segmenting overlapping cytoplasm in a medical image can obtain more accurate results more effectively.

BRIEF DESCRIPTION OF THE DRAWINGS

The technical solution of the present invention can be better understood through the drawings and the following description, in which.

DETAILED DESCRIPTION

According to the present invention, all overlapping cytoplasm in a clump is segmented by evolving the cytoplasm shape guided by the modeled local prior shape and overall prior shape and simultaneously evolving the mutual shape constraints of the cytoplasm, so that the shape prior-based method of the present invention for segmenting overlapping cytoplasm in an medical image can accurately and efficiently obtain cytoplasm segmentation results, thereby improving the accuracy and efficiency of cervical cancer screening. Specifically, by using statistical shape information to model local prior shapes, shape hypothesis set with infinite cytoplasm shape hypothesis is established; in the multi-shape evolution step, in addition to considering the local prior shapes, the present invention obtains the overall prior shape by evolving the shape of the cytoplasm and then using an algorithm to make the segmentation result consistent with the clump evidence. In addition, in the multi-shape evolution step, the final shape obtained in the evolution process is required to be within the shape hypothesis set, thereby reducing the incredible segmentation results in the prior art. Moreover, in order to make the established shape hypothesis better restore any invisible cytoplasm shape, the present invention also adds a step of learning the importance of shape instances in the shape statistics calculation.

Figure 1B:
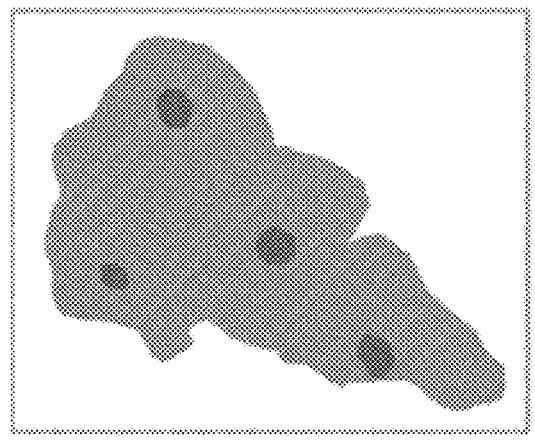
FIGS. 1a to 1d show schematic diagrams of segmentation of a clump with overlapping cytoplasm according to a method of the present invention.
Figure 1A:
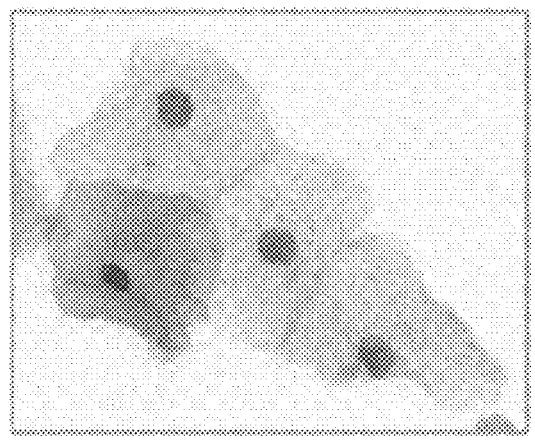
Figure 1D:
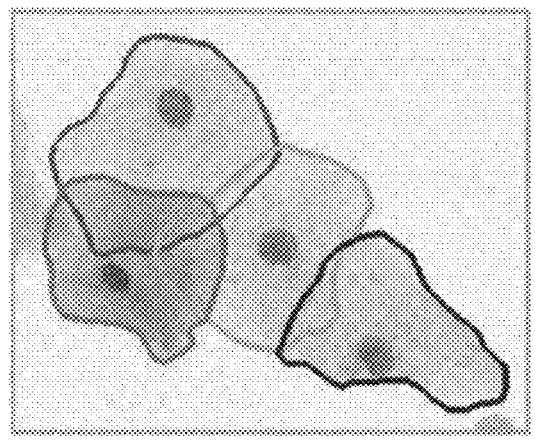
Figure 1C:
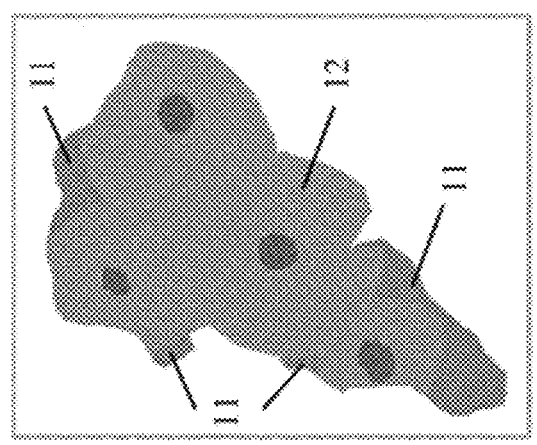
Figure 2:
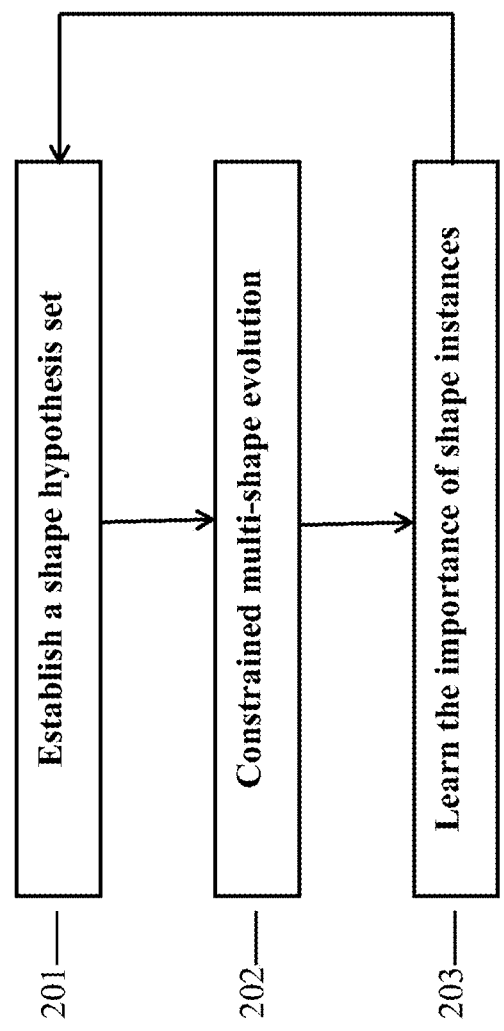
FIG. 2 shows a flowchart of a method of the present invention.

The present invention adopts the following new algorithms and steps to implement a new method for segmenting a clump with overlapping cytoplasm in a medical image. FIGS. 1a-1d show schematic diagrams of segmenting a clump with overlapping cytoplasm using the method of the present invention. FIG. 1a shows an image of an input clump, FIG. 1b shows an initially segmented clump area. FIG. 1c shows deviation areas 11 in a random evolution and an area 12 covered by all aligned shapes. FIG. 1d shows segmentation results obtained by the method of the present invention. FIG. 2 shows a flowchart of a method of the present invention. The method includes three steps: step 201 of establishing a shape hypothesis set, step 202 of constrained multi-shape evolution, and step 203 of learning the importance of shape instances.

The following content provides a detailed description of the above-mentioned three steps: step 201 of establishing a shape hypothesis set, step 202 of constrained multi-shape evolution, and step 203 of learning the importance of shape instances.

Establishing a Shape Hypothesis Set

First, the shape of the cytoplasm of the cell is parameterized. Boundary points in the form of vector s are used to describe the shape of the cytoplasm of each cell. The k-th s stores a distance value of the boundary point having an angle value equal to k in a polar coordinate system, and the origin of the polar coordinate system is located at the center of mass of a cell nucleus. It should be noted that each cell is composed of a cytoplasm and a nucleus. In the present invention, the center of mass of a cell nucleus rather than the center of mass of the cytoplasm is selected as the origin of the polar coordinate system for the consideration of feasibility, because it is easier to detect the center of mass of the cell nucleus than to detect the center of mass of the cytoplasm when the cytoplasm of cells overlaps (see FIG. 1a).

In addition, according to the existing method of establishing an infinite shape hypothesis set in the prior art, the shape hypothesis set is established by using the statistical shape information of the cytoplasm. In the present invention, the shape hypothesis set is expressed as follows:

$$\mathcal{H}_s = \{s_i : s_i = \mu + Mx_i, i \in \mathbb{N}\} \tag{1}$$

where $\mu$ represents an average shape of collected shape instances, $Mx_i$ represents a linear combination of eigenvectors of a covariance matrix of the collected shapes (wherein each column of the matrix M represents an eigenvector and $x_i$ represent a weight vector of the linear combination), and $s_i$ represents a shape hypothesis marked as i.

By substituting $x_i$ of different values into formula (1), different shape hypotheses $s_i$ can be obtained. Since an infinite number of $x_i$ can be selected, an infinite shape hypothesis set can be established. However, relying on the shape hypothesis set established by formula (1), it is difficult to collect shape instances that can well restore invisible cytoplasm shapes. The present invention overcomes this shortcoming by implementing the following step of learning the importance of shape instances in the calculation of shape statistics.

Constrained Multi-Shape Evolution

Figure 3:
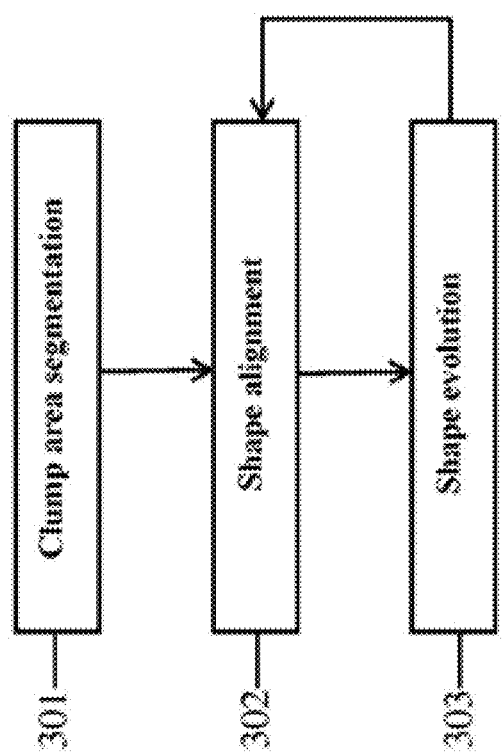
FIG. 3 shows a flowchart of a constrained multi-shape evolution step of the present invention.

FIG. 3 shows a flowchart of constrained multi-shape evolution of the present invention. The constrained multi-shape evolution step of the present invention is to segment overlapping cytoplasm based on clump evidence and by selecting a shape hypothesis for each cytoplasm from an established shape hypothesis set. The constrained multi-shape evolution consists of three steps: clump area segmentation for providing clump evidence (step 301); shape alignment for evaluating the quality of the current shape hypothesis (step 302); and shape evolution for finding a better shape hypothesis for each cytoplasm (step 303). The shape alignment (step 302) and shape evolution (step 303) are performed iteratively. The shape evolution (step 303) takes the result of shape alignment as input and the output of shape evolution (step 303) as the input of shape alignment to detect whether to start a new shape evolution or not. Once it is determined that no new shape evolution is required, the current shape hypothesis after the shape alignment is regarded as a segmentation result of the cytoplasm (see FIG. 1d).

In the clump area segmentation (step 301), the present invention uses a multi-size convolutional neural network (CNN) to segment cytoplasm and nucleus areas (see FIG. 1b). The multi-size CNN divides each pixel in an image into three groups: nucleus part, cytoplasm part, and background part. Three parallel CNNs are included, each CNN has different sizes in terms of the resolution of an input patch. The outputs of these three CNNs are then fused to help capture more contextual information in different sizes. Finally, Markov random field is used to further optimize the segmentation result.

In the shape alignment (step 302), for the shape hypothesis $s_i$, since it is only a vector storing boundary point information, a corresponding binary image of $s_i$ (i.e. binary image) is obtained by filling an area inside a contour described by $s_i$. Pixels inside the contour are marked as 1, and pixels outside the contour are marked as 0. As described above, $s_i$ is assigned as the output of the shape evolution step, and the average shape of the instances collected from the shape hypothesis set is used as the initial $s_i$ of each cytoplasm. In addition, since the present invention can circumvent non-rigid transformation through the evolution of shape hypothesis described below, the present invention limits the shape alignment to rigid alignment.

Specifically, for each $s_i$, first the center of mass of an area where $s_i$ is filled, is aligned with the center of mass of the cell nucleus in the image. Then, a scaling factor ($r_i$) and a rotation coefficient $\theta_i$ for alignment are obtained with a formula as follows:

$$\mathrm{argmax}(B_i \cap B_c), \ s.\ t.\ B_i \subset B_c \tag{2}$$

where: $B_c$ represents an image of the segmented clump area; $B_i$ represents the alignment result, which is obtained by rotating the area where $s_i$ is filled by an angle $\theta_i$ and scaling it with the number $r_i$; $B_i$ is a binary image with the same size as $B_c$, where the values of $r_i$ and $\theta_i$ are determined by grid search.

The alignment result $B_i$ should be inside $B_c$. If there is no such constraint, the shape hypothesis actually obtained is aligned with the entire clump area, rather than aligned with the cytoplasm itself.

In the shape evolution (step 303), for the alignment result $B_i$, the shape evolution algorithm of the present invention can find a more suitable cytoplasm shape hypothesis than $s_i$. First, an objective function as shown in the following formula (3) needs to be defined:

$$\mathbb{E}(B_c, x^k) = \sum_{(x,y) \in \Omega_B} (B_g(x,y) - B_c(x,y))^2 \tag{3}$$

where x represents set $\{x_i\}_{i=1}^{N}$, $x^k$ represents x of the k-th evolution, as described in formula (1), $s_i$ is determined by $x_i$; N represents quantity of cytoplasm in the clump; $B_g = \cup_{i=1}^{N} B_i$ represents a binary image generated by the alignment result $\{B_i\}_{i=1}^{N}$; (x, y) represents coordinates of a pixel in the image.

It can be seen that the objective function represented by the formula (3) is actually to detect the difference about pixel between a segmented clump area and a clump area composed of the alignment result. In an ideal state, if all the cytoplasm is segmented very accurately, $\mathbb{E}$ is equal to 0. As mentioned above, this ideal state is difficult to achieve. Therefore, the objective function is designed in the method of the present invention. The main reason is to make full use of the boundary information of the clump while minimizing the influence of insufficient intensity information in the overlapping area.

Therefore, according to the present invention, $x^{k+1}$ that causes $\mathbb{E}$ to have a value lower than $x^k$ is found through the following formulas (4) to (6). For any matrix p obtained from formula (3), the following formula (4) is obtained here using Taylor's theorem:

$$\mathbb{E}\,(x^k+p) = \mathbb{E}\,(x^k) + \nabla\,\mathbb{E}\,(x^k)^T p + \tfrac{1}{2} p^T \nabla^2\,\mathbb{E}\,(x^k+\gamma p)p \tag{4}$$

where $\nabla$ and $\nabla^2$ respectively represent a gradient and Hessian matrix calculation; $\gamma$ is a certain scalar in the interval (0, 1). The above formula (4) indicates that only information about the function value, the first derivative and the second derivative at $x^k$ can be used to approximate $\mathbb{E}$ near $x^k$, so as to obtain the minimum value of the overall area of $\mathbb{E}$ in an area formed with $x^k$ as the center of a circle and $\|p\|_2$ as a radius.

In theory, the minimum value of the overall area is the optimal $x^{k+1}$ that can be used in the k-th evolution. However, since the value of the scalar $\gamma$ is unknown, $\mathbb{E}$ cannot be obtained directly by analysis. Therefore, the process returns to $x^k$ to approximate $\mathbb{E}$, $\mathbb{E}$ at $x^k$ is represented by $m_k$ in the following formula (5):

$$m_k(p) = \mathbb{E}\,(x^k) + \nabla\,\mathbb{E}\,(x^k)^T p + \tfrac{1}{2} p^T \nabla^2\,\mathbb{E}\,(x^k)p. \tag{5}$$

When $\|p\|_2$ is very small, the result is very accurate with an approximate error of $\mathcal{O}\,(\|p\|_2^3)$, and then the minimum value of $\mathbb{E}$ is approximated by the minimum value of $m_k$ as follows:

$$p^* = \underset{p \in \Omega_p}{\mathrm{argmin}}\, m_k(p),\ \text{s.t.}\ \|p\|_2 \le \Delta_k. \tag{6}$$

The formula (6) can be solved by the existing trust region method (see J. Nocedal and S J Wright. *Numerical Optimization*. Springer, 2006), and finally, the output result of the k-th evolution is shown in formula (7):

$$x^{k+1} = x^k + p^*. \quad (7)$$

Once $x^{k+1}$ is obtained, the new shape hypothesis is aligned with the image, and then a new evolution calculation starts until $\mathbb{E}$ cannot decrease any more or reaches a predetermined threshold $\mathbb{E}^*$. For the cytoplasm i, the final shape hypothesis $s_i$ after alignment is regarded as a final segmentation result.

Learning the Importance of Shape Instances

In order to better restore any invisible cytoplasm shape by the shape hypotheses in the shape hypothesis set $\mathcal{H}_s$ calculated according to the above formula (1), the present invention also adopts the step 203 of learning the importance of shape instances in the shape statistics calculation. The method of the present invention for learning the importance of shape instances can solve a series of problems caused by manual collection of shape instances in the prior art.

Specifically, a set of K input-output pairs are selected randomly first, as shown in the following formula (8):

$$\mathcal{D} = \{B_c^j, \{s_i^j\}_{i=1}^{N_j}\}_{j=1}^K \quad (8)$$

where $B_c^j$ represents the image, in the training image j, in which the clump area is segmented; $s_i^j$ represents a shape vector of the cytoplasm i in the image j; $N_j$ represents quantity of cytoplasm in the image j. $\mathcal{D}$ is obtained from the above formula (8), and a small set of shape instances $\{s_i\}_{i=1}^{K_s}$ are selected. Each instance $s_i$ initially has an importance, represented by $\omega_i$. Then, the average shape is calculated with the following formula (9):

$$\mu = \frac{1}{W} \sum_{i=1}^{K_s} \omega_i s_i \quad (9)$$

where W represents the sum of all $\omega_i$. Then, the covariance matrix is calculated with the following formula (10):

$$M_c = \frac{1}{K_s} \sum_{i=1}^{K_s} (s_i - \mu)(s_i - \mu)^T \quad (10)$$

where the first t eigenvectors of the matrix $M_c$ constitute matrix $M = (e_1 \ e_2 \ \ldots \ e_t)$, and their corresponding eigenvalues are $\lambda_1 \geq \lambda_2 \geq \ldots \geq \lambda_t$.

The correlation between the step 203 of learning the importance of shape instances and the above-mentioned constrained multi-shape evolution step 202 and step 201 of establishing a shape hypothesis set (see FIG. 2) is as follows: in each training image $B_c^j$, according to the initial μ and M in the step of establishing the shape hypothesis set, the constrained multi-shape evolution step is performed, and then the final $\mathbb{E}_j$ is detected. If $\mathbb{E}_j$ is greater than the predetermined threshold $\mathbb{E}^*$, the current μ and M are not ideal. Therefore, recalculation is required according to the formulas (9) and (10) in the step of learning the importance of the shape instances to increase $\{s_i^j\}_{i=1}^{N_j}$, thereby updating μ and M in the shape hypothesis set. In the update process, the importance $w_i^j$ of each shape instance is determined by grid search. The above step of increasing $\{s_i^j\}_{i=1}^{N_j}$ is continued until $\mathbb{E}_j$ starts to decrease. The entire step of learning the importance of shape instances is repeated in $\mathcal{D}$ in accordance with formula (8) until the sum of all final differences $$\sum_{i=1}^K \mathbb{E}_j$$

does not decrease any more.

Figure 4:
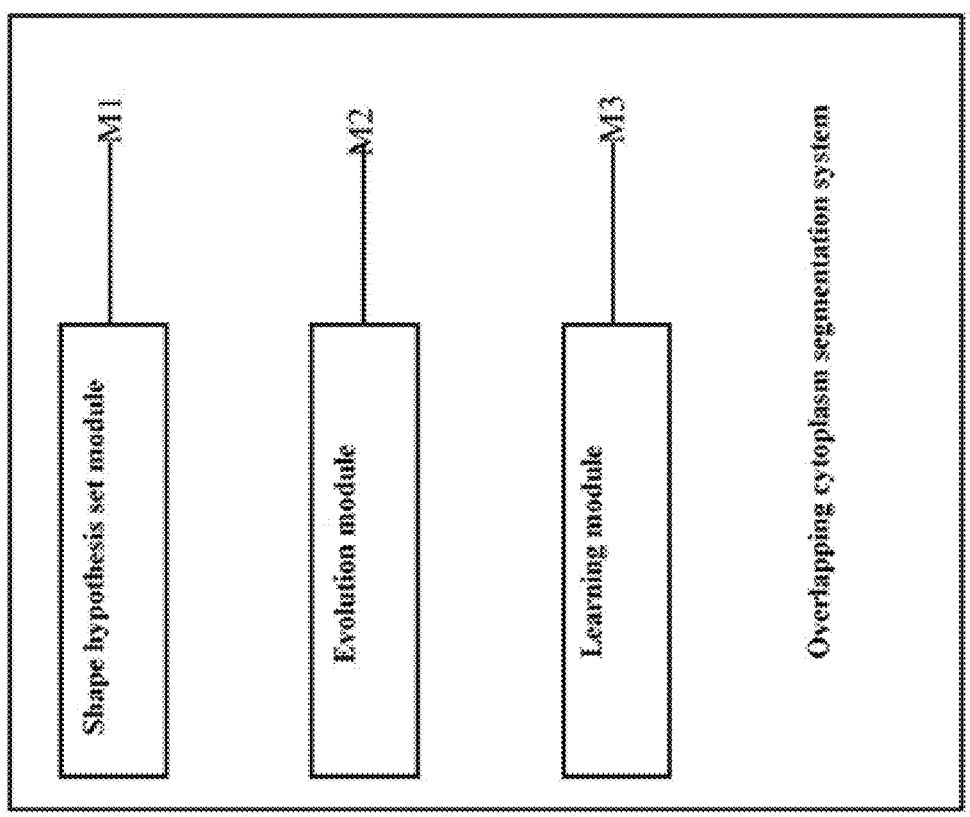
FIG. 4 shows a schematic diagram of an overlapping cytoplasm segmentation system of the present invention.

As shown in FIG. 4, the present invention also relates to an overlapping cytoplasm segmentation system, including: a shape hypothesis set module M1 configured to establish a shape hypothesis set, an evolution module M2 configured to perform constrained multi-shape evolution, and a learning module M3 configured to learn the importance of shape instances. First, the shape hypothesis set module M1 provides initial μ and M, and then the constrained multi-shape evolution is performed in the evolution module M2, and then the final $\mathbb{E}_j$ is detected. If $\mathbb{E}_j$ is greater than the predetermined threshold $\mathbb{E}^*$, it means that the current μ and M are not ideal. Therefore, recalculation is required to perform in the learning module M3 according to the above formulas (9) and (10) to increase $\{s_i^j\}_{i=1}^{N_j}$, thereby updating μ and M in the shape hypothesis set. The above step of increasing $\{s_i^j\}_{i=1}^{N_j}$ is continued until $\mathbb{E}_j$ starts to decrease.

EXAMPLE

This example is based on two typical cervical scraping data sets: Pap stain data set and H&E stain data set. For obtaining the Pap stain data set, reference is made to (Z. Lu, G. Carneiro, A. Bradley et al., "Evaluation of three algorithms for the segmentation of overlapping cervical cells", *IEEE Journal of Biomedical and Health Informatics*, 21(2): 441-450, 2017). This data set includes 8 publicly available images, and each image has 11 clumps with an average of 3.3 cytoplasm instances. The H&E stain data set is prepared by H&E staining; the data set includes 21 images, and each image has 7 clumps with an average of 6.1 cytoplasm instances.

First, a training set $\mathcal{D}$ is constructed using three images randomly selected from the Pap stain data set and five images randomly selected from the H&E stain data set, and the remaining images form a test set. The training set $\mathcal{D}$ has 72 clumps and 324 cytoplasm instances, of which 28 isolated cytoplasm instances are used to initialize a small shape instance set $\{s_i\}_{i=1}^{K_s}$. There are 184 clumps containing 907 cytoplasm instances in the test set, and the number of cytoplasm instances in each clump is 2 to 13 (the average is 4.93, and the standard deviation is 1.81).

In the method of the present invention, two parameters need to be set: a predetermined threshold $\mathbb{E}^*$ for terminating the multi-shape evolution step, and a value for calculating the eigenvector t of the matrix M. Although usually small $\mathbb{E}^*$ helps to improve the accuracy of the segmentation result, a smaller $\mathbb{E}^*$ causes longer calculation time. In the present invention, in order to balance the accuracy of the segmentation result and the calculation time, the predetermined threshold $\mathbb{E}^*$ is set to be approximately between 3% and 7% of the number of pixels in the clump, preferably approximately 5%. For the value of the eigenvector t, a larger t will make the assessed shape $s_i$ show more details of the overall shape, but it will also consume more computing resources in the shape evolution process. In the present invention, t is determined on the basis of the existing formula $(\sum_{i=1}^t \lambda_i / \sum \lambda_i) > 0.995$ disclosed in the prior art (see T F Cootes, C J Taylor, D H Cooper, etc., "Active shape models-their training and application", *Computer Vision and Image Understanding*, 61(1):38-59, 1995), and the value of t is set to be 20 in this example.

In this embodiment, the results obtained by the method according to the present invention are compared with those of four existing technologies (see Table 1 below). The four existing technologies are joint level set function method (see Z. Lu, G. Carneiro and A P Bradley. "An improved joint optimization of multiple level set functions for the segmentation of overlapping cervical cells", *IEEE Transactions on Image Processing*, 24(4):1261-1272, 2015.), multi-cell labeling (see Y. Song, E L Tan, X. Jiang, etc., "Accurate cervical cell segmentation from overlapping clumps in pap smear images", *IEEE Transactions on Medical Imaging*, 36(1):288-300, 2017), multi-pass watershed method (see A. Tareef, Y. Song, H. Huang, etc., "Multi-pass fast watershed for accurate segmentation of overlapping cervical cells", *IEEE Transactions on Medical Imaging*, 2018.) and contour segmentation method (see Y. Song, J. Qin, B. Lei, etc., "Automated segmentation of overlapping cytoplasm in cervical smear images via contour fragments", In *Proceedings of the 32th AAAI Conference on Artificial Intelligence*, pages 168-175. AAAI, 2018.). In Table 1, LSF, MCL, MPW, and CF are used to represent the segmentation results of the above four existing technologies, wherein LSF, MCL and CF belong to the existing shape prior-based methods, and MPW is a variant of the watershed method.

TABLE 1

| | Pap stain data set | | | | | H&E stain data set | | | | |
|---|---|---|---|---|---|---|---|---|---|---|
| | $[0, 1/4)$ | $[1/4, 2/4)$ | $[2/4, 3/4)$ | $[3/4, 1)$ | Total | $[0, 1/4)$ | $[1/4, 2/4)$ | $[2/4, 3/4)$ | $[3/4, 1)$ | Total |
| LSF | 0.81 | 0.77 | 0.74 | 0.71 | 0.77 | 0.80 | 0.75 | 0.72 | 0.69 | 0.75 |
| MCL | 0.80 | 0.79 | 0.77 | 0.72 | 0.78 | 0.81 | 0.76 | 0.72 | 0.70 | 0.76 |
| MPW | 0.82 | 0.80 | 0.77 | 0.73 | 0.79 | 0.81 | 0.79 | 0.74 | 0.71 | 0.78 |
| CF | 0.84 | 0.82 | 0.79 | 0.77 | 0.81 | 0.83 | 0.81 | 0.79 | 0.75 | 0.80 |
| Present invention | 0.85 | 0.83 | 0.82 | 0.81 | 0.83 | 0.84 | 0.83 | 0.82 | 0.80 | 0.82 |

Table 1 lists the quantitative comparison of the segmentation results obtained by different methods under multiple overlap conditions. The overlap is used to measure the degree of overlap and calculated by the length ratio of the occluded boundary part to the entire boundary part of the cytoplasm. From the results in Table 1, it can be seen that the method of the present invention obtains the optimal segmentation results, and compared with other methods, the accuracy of the method of the present invention has an improvement of about 5% on average. Specifically, when the overlap is less than 0.5 (see columns [0, 1/4) and [1/4, 2/4) in the table), the accuracy of the method of the present invention has an improvement of about 3% on average; when the overlap is greater than 0.5 (see columns [2/4, 3/4) and [3/4, 1) in the table), the accuracy of the method of the present invention has an improvement of about 8% on average.

Figure 5:
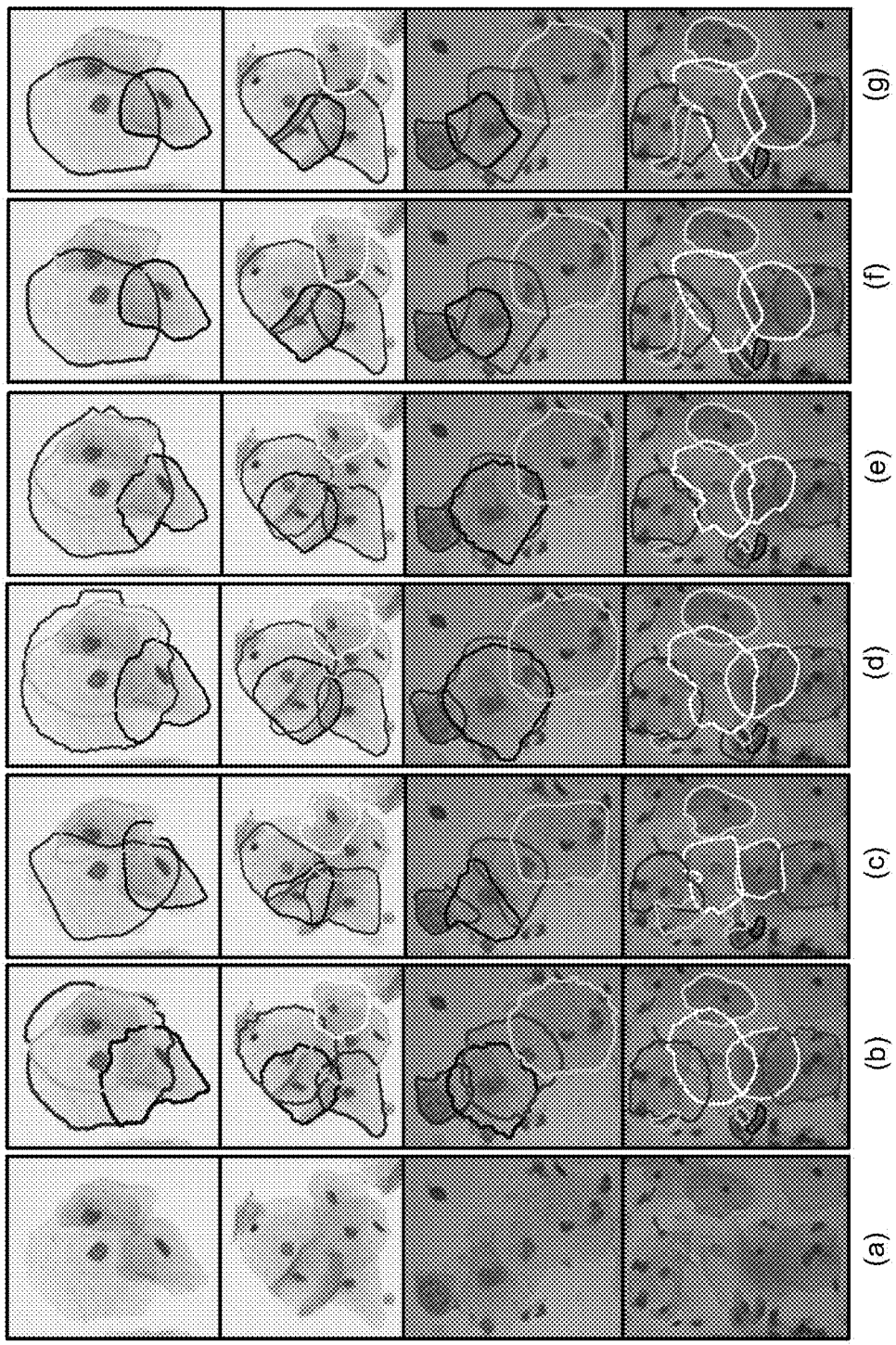
FIG. 5 shows comparison images of the segmentation results obtained according to a method of the present invention and methods in the prior art.

In addition, FIG. 5 shows a comparison image of the segmentation results obtained according to the method of the present invention and methods in the prior art. FIG. 5-(a) shows the original input image, FIG. 5-(b) to FIG. 5-(f) respectively show the images of the segmentation results obtained by LSF, MCL, MPW, CF and the method of the present invention, respectively; FIG. 5-(g) shows the actual segmentation image. It can be seen more intuitively from FIG. 5 that the segmentation method of the present invention (as shown in FIG. 5-(f)) obtains the optimal segmentation results. For some of the cytoplasm instances therein, their segmentation results are even consistent with the actual segmentation results (as shown in FIG. 5-(g)).

The method and system of the present invention overcome the problem that the cytoplasm cannot be accurately segmented due to lack of intensity information in the overlapping area. Compared with the existing shape prior-based technologies, the method and system of the present invention provide a more accurate method and system for segmenting cytoplasm in an overlapping area by establishing an infinite shape hypothesis set, calculating and evolving local prior shapes and overall prior shapes, and imposing shape constraints on the final result.

The method and system of the present invention are not limited to the detection of cervical cancer, and those skilled in the art can make appropriate improvements so that the method and system of the present invention can be applied to other microscopy images that quantitatively measure cell-level features, such as pathological image measurement.

Although the present invention has been described above with reference to the specific embodiments of the shape priori-based method and system for detecting overlapping cytoplasm, it is certainly conceivable that a person of ordinary skill in the art can derive many variants. Therefore, variations readily conceivable by those of ordinary skill in the art are considered as part of the present invention. The scope of the present invention is defined in the appended claims.

What is claimed is:

1. A method for segmenting overlapping cytoplasm in a medical image comprising:
   establishing a cytoplasm shape hypothesis set; and
   selecting a shape hypothesis for each cytoplasm from the established cytoplasm shape hypothesis set to perform constrained multi-shape evolution, thereby segmenting overlapping cytoplasm in the medical image, wherein the constrained multi-shape evolution comprises the following steps:
      clump area segmentation performed to segment a clump area composed of a plurality of overlapping cytoplasm in the medical image to provide clump evidence;
      shape alignment performed to assess quality of the selected shape hypothesis; and
      shape evolution performed to determine a better shape hypothesis for each cytoplasm;
   wherein the shape alignment and the shape evolution are performed iteratively, an output of the shape alignment is used as an input of the shape evolution, and an output of the shape evolution is used as an input of the shape alignment; the shape alignment assesses whether to start a new shape evolution or not, and once it is determined that no new shape evolution is required, a current shape hypothesis after the shape alignment is regarded as a segmentation result of the overlapping cytoplasm;

wherein the cytoplasm shape hypothesis set is established with a formula as follows:

$$\mathcal{H}_s = \{s_i : s_i = \mu + Mx_i, i \in \mathbb{N}\}$$

where μ represents an average shape of collected shape instances, $Mx_i$ represents a linear combination of eigenvectors of a covariance matrix of the collected shapes, wherein each column of the matrix M represents an eigenvector, $x_i$ represents a weight vector of the linear combination, and $s_i$ represents a shape hypothesis marked as i; and wherein the shape alignment comprises filling the shape hypotheses selected from the cytoplasm shape hypothesis set to obtain a binary image, and obtaining a rotation angle and a scaling size required for aligning the binary image with the corresponding cytoplasm with a formula as follows:

$$\mathrm{argmax}(B_i \cap B_c),\ s.\ t.\ B_i \subset B_c$$

where $B_c$ represents an image of the segmented clump area; $B_i$ represents an alignment result image, $B_i$ is a binary image with the same size as $B_c$, and $B_i$ should be inside $B_c$.

2. The method according to claim 1 further comprising a step of learning the importance of shape instances for updating cytoplasm shape instances for the established cytoplasm shape hypothesis set.

3. The method according to claim 2, wherein the step of learning the importance of shape instances comprises:

randomly selecting a set of shape instances and calculating an average shape of the set of shape instances with a formula as follows:

$$\mu = \frac{1}{W} \sum_{i=1}^{K_s} \omega_i s_i$$

where $K_s$ represents a number of selected shape instances; $\omega_i$ represents the importance of each shape instance $s_i$; W represents a sum of all $\omega_i$; and calculating the covariance matrix according to the obtained μ as follows:

$$M_c = \frac{1}{K_s} \sum_{i=1}^{K_s} (s_i - \mu)(s_i - \mu)^T$$

where a first t eigenvectors of the matrix $M_c$ constitute a matrix $M = (e_1\ e_2\ \ldots\ e_t)$, and their corresponding eigenvalues are $\lambda_1 \geq \lambda_2 \geq \ldots \geq \lambda_t$.

4. The method according to claim 3, wherein if the segmentation result obtained by the constrained multi-shape evolution is greater than a predetermined threshold, recalculation is performed by the step of learning the importance of shape instances to update the shape hypothesis set; and the update is stopped until the segmentation result cannot decrease any more or reaches the predetermined threshold.

5. The method according to claim 1, wherein the shape evolution comprises:

setting an objective function, the objective function being as follows:

$$\mathbb{E}(B_c, x^k) = \sum_{(x,y) \in \Omega_B} (B_g(x,y) - B_c(x,y))^2$$

where x represents set $\{x_i\}_{i=1}^N$ and $x^k$ represents x in the k-th evolution; N represents quantity of cytoplasm in the clump area; $B_g = \cup_{i=1}^N B_i$ represents a binary image generated by an alignment result $\{B_i\}_{i=1}^N$; (x, y) represents coordinates of a pixel in the image; and determining $x^{k+1}$ that causes $\mathbb{E}$ to have a lower value than $x^k$.

6. The method according to claim 5, wherein the determining of $x^{k+1}$ that causes $\mathbb{E}$ to have a lower value than $x^k$ comprises:

for matrix p obtained from the objective function, obtaining the following formula according to Taylor's theorem:

$$\mathbb{E}_{(x^k+p)} = \mathbb{E}_{(x^k)} + \nabla \mathbb{E}_{(x^k)}^T p + \tfrac{1}{2} p^T \nabla^2 \mathbb{E}_{(x^k + \gamma p)} p$$

where $\nabla$ and $\nabla^2$ respectively represent a gradient and Hessian matrix calculation; γ represents a scalar in an interval (0, 1), and then a minimum value of an overall area of $\mathbb{E}$ in an area formed with $x^k$ as a center of a circle and $\|p\|_2$ as a radius is obtained;

returning to $x^k$ to approximate $\mathbb{E}$ as follows:

$$m_k(p) = \mathbb{E}_{(x^k)} + \nabla \mathbb{E}_{(x^k)}^T p + \tfrac{1}{2} p^T \nabla^2 \mathbb{E}_{(x^k)} p$$

where $m_k$ represents $\mathbb{E}$ at $x^k$;

approximating the minimum value of $\mathbb{E}$ by the minimum value of $m_k$, and solving the following formula by a trust region method:

$$p^* = \underset{p \in \Omega_p}{\mathrm{argmin}} m_k(p),\ \mathrm{s.t.}\ \|p\|_2 \leq \Delta_k;$$

and obtaining an output result of the k-th evolution as follows:

$$x^{k+1} = x^k + p^*.$$

7. A system for segmenting overlapping cytoplasm in a medical image comprising:

a shape hypothesis set module configured to establish a cytoplasm shape hypothesis set; and an multi-shape evolution module configured to select a shape hypothesis for each cytoplasm from the established cytoplasm shape hypothesis set to perform constrained multi-shape evolution, thereby segmenting overlapping cytoplasm in the medical image, wherein the multi-shape evolution module is configured to perform:

clump area segmentation to segment a clump area composed of a plurality of overlapping cytoplasm in the medical image to provide clump evidence;

shape alignment to assess quality of the selected shape hypothesis; and shape evolution to determine a better shape hypothesis for each cytoplasm;

wherein the shape alignment and the shape evolution are performed iteratively, an output of the shape alignment is used as an input of the shape evolution, and an output of the shape evolution is used as an input of the shape alignment; the shape alignment assesses whether to start a new shape evolution or not, and once it is determined that no new shape evolution is required, a current shape hypothesis after the shape alignment is regarded as a segmentation result of the overlapping cytoplasm;

wherein the cytoplasm shape hypothesis set is established with a formula as follows:

$$\mathcal{H}_s = \{s_i : s_i = \mu + Mx_i, i \in \mathbb{N}\}$$

where $\mu$ represents an average shape of collected shape instances, $Mx_i$ represents a linear combination of eigenvectors of a covariance matrix of the collected shapes, wherein each column of the matrix M represents an eigenvector, $x_i$ represents a weight vector of the linear combination, and $s_i$ represents a shape hypothesis marked as i; and wherein the shape alignment comprises filling the shape hypotheses selected from the cytoplasm shape hypothesis set to obtain a binary image, and obtaining a rotation angle and a scaling size required for aligning the binary image with the corresponding cytoplasm with a formula as follows:

$$\operatorname{argmax}(B_i \cap B_c), \text{ s. t. } B_i \subset B_c$$

where $B_c$ represents an image of the segmented clump area; $B_i$ represents an alignment result image, $B_i$ is a binary image with the same size as $B_c$, and $B_i$ should be inside $B_c$.

8. The system according to claim 7, wherein the shape involution comprises:

setting an objective function, the objective function being as follows:

$$\mathbb{E}(B_c, x^k) = \sum_{(x,y) \in \Omega_B} (B_g(x,y) - B_c(x,y))^2$$

where x represents set $\{x_i\}_{i=1}^N$ and $x^k$ represents x in the k-th evolution; N represents quantity of cytoplasm in the clump area; $B_g = \cup_{i=1}^N B_i$ represents a binary image generated by an alignment result $\{B_i\}_{i=1}^N$; (x, y) represents coordinates of a pixel in the image; and determining $x^{k+1}$ that causes $\mathbb{E}$ to have a lower value than $x^k$.

9. The system according to claim 8, wherein the determining of $x^{k+1}$ that causes $\mathbb{E}$ to have a lower value than $x^k$ comprises:

for matrix p obtained from the objective function, obtaining the following formula according to Taylor's theorem:

$$\mathbb{E}(x^k+p) = \mathbb{E}(x^k) + \nabla \mathbb{E}(x^k)^T p + \tfrac{1}{2} p^T \nabla^2 \mathbb{E}(x^k+\gamma p) p$$

where $\nabla$ and $\nabla^2$ respectively represent a gradient and Hessian matrix calculation; $\gamma$ represents a scalar in an interval (0, 1), and then a minimum value of an overall area of $\mathbb{E}$ in an area formed with $x^k$ as a center of a circle and $\|p\|_2$ as a radius is obtained;

returning to $x^k$ to approximate $\mathbb{E}$ as follows:

$$m_k(p) = \mathbb{E}(x^k) + \nabla \mathbb{E}(x^k)^T p + \tfrac{1}{2} p^T \nabla^2 \mathbb{E}(x^k) p$$

where $m_k$ represents $\mathbb{E}$ at $x^k$;

approximating the minimum value of $\mathbb{E}$ by the minimum value of $m_k$, and solving the following formula by a trust region method:

$$p^* = \operatorname*{argmin}_{p \in \Omega_p} m_k(p), \text{ s.t. } \|p\|_2 \leq \Delta_k;$$

and obtaining an output result of the k-th evolution as follows:

$$x^{k+1} = x^k + p^*.$$

10. The system according to claim 7 further comprising a shape instance importance learning module configured to update cytoplasm shape instances for the established cytoplasm shape hypothesis set.

11. The system according to claim 10, wherein the shape instance importance learning module is configured to:

randomly select a set of shape instances and calculating an average shape of the set of shape instances with a formula as follows:

$$\mu = \frac{1}{w} \sum_{i=1}^{K_s} \omega_i s_i$$

where $K_s$ represents a number of selected shape instances; $\omega_i$ represents the importance of each shape instance $s_i$; W represents a sum of all $\omega_i$; and calculate the covariance matrix according to the obtained $\mu$ as follows:

$$M_c = \frac{1}{K_s} \sum_{i=1}^{K_s} (s_i - \mu)(s_i - \mu)^T$$

where a first t eigenvectors of the matrix $M_c$ constitute a matrix $M = (e_1\ e_2\ \ldots\ e_t)$, and their corresponding eigenvalues are $\lambda_1 \geq \lambda_2 \geq \ldots \geq \lambda_t$.

12. The system according to claim 11, wherein if the segmentation result obtained by the constrained multi-shape evolution module is greater than a predetermined threshold, recalculation is performed by the shape instance importance learning module to update the shape hypothesis set; and the update is stopped until the segmentation result cannot decrease any more or reaches the predetermined threshold.

13. A method for segmenting overlapping cytoplasm in a medical image comprising:

establishing a cytoplasm shape hypothesis set;

a step of learning the importance of shape instances for updating cytoplasm shape instances for the established cytoplasm shape hypothesis set, wherein the step of learning the importance of shape instances comprises:

randomly selecting a set of shape instances and calculating an average shape of the set of shape instances with a formula as follows:

$$\mu = \frac{1}{W} \sum_{i=1}^{K_s} \omega_i s_i$$

where $K_s$ represents a number of selected shape instances; $\omega_i$ represents the importance of each shape instance $s_i$; W represents a sum of all $\omega_i$; and calculating the covariance matrix according to the obtained μ as follows:

$$M_c = \frac{1}{K_s}\sum_{i=1}^{K_s}(s_i - \mu)(s_i - \mu)^T$$

where a first t eigenvectors of the matrix $M_c$ constitute a matrix $M=(e_1\ e_2 \ldots e_t)$, and their corresponding eigenvalues are $\lambda_1 \geq \lambda_2 \geq \ldots \geq \lambda_t$;

and selecting a shape hypothesis for each cytoplasm from the established cytoplasm shape hypothesis set to perform constrained multi-shape evolution, thereby segmenting overlapping cytoplasm in the medical image, wherein the constrained multi-shape evolution comprises the following steps:

clump area segmentation performed to segment a clump area composed of a plurality of overlapping cytoplasm in the medical image to provide clump evidence;

shape alignment performed to assess quality of the selected shape hypothesis; and shape evolution performed to determine a better shape hypothesis for each cytoplasm.

14. The method according to claim 13, wherein if the segmentation result obtained by the constrained multi-shape evolution is greater than a predetermined threshold, recalculation is performed by the step of learning the importance of shape instances to update the shape hypothesis set; and the update is stopped until the segmentation result cannot decrease any more or reaches the predetermined threshold.

\* \* \* \* \*